United States Patent [19]

Tanihara et al.

[11] Patent Number: 5,132,402
[45] Date of Patent: * Jul. 21, 1992

[54] ADSORBENT, METHOD FOR PRODUCTION THEREOF, AND METHOD FOR USE THEREOF

[75] Inventors: Masao Tanihara; Kiichiro Oka; Hideaki Yamada; Akira Kobayashi, all of Kurashiki; Toshihide Nakashima, Toyonaka; Yoshiaki Omura, Okayama; Koichi Takakura, Nishinomiya, all of Japan

[73] Assignees: Agency of Industrial Science & Technology; Ministry of International Trade & Industry, Tokyo, Japan

[*] Notice: The portion of the term of this patent subsequent to Dec. 26, 2006 has been disclaimed.

[21] Appl. No.: 265,540

[22] Filed: Nov. 1, 1988

[30] Foreign Application Priority Data

Nov. 25, 1987 [JP] Japan ................................ 62-295369

[51] Int. Cl.$^5$ ....................... A61K 37/02; C07K 5/00; C07K 7/00
[52] U.S. Cl. ..................... 530/326; 514/13; 514/12; 530/324; 530/325; 124/400
[58] Field of Search ............... 435/4, 7.5; 436/501, 436/504; 530/324, 325, 326, 327; 514/13, 12; 424/400

[56] References Cited

U.S. PATENT DOCUMENTS

| 4,433,058 | 2/1984 | Deutsch | 436/504 |
| 4,889,917 | 12/1989 | Tanihara et al. | 530/324 |
| 4,925,787 | 5/1990 | Tanihara et al. | 435/7 |
| 5,001,048 | 3/1991 | Taylor et al. | 435/4 |

FOREIGN PATENT DOCUMENTS 0172580 2/1986 European Pat. Off. .
8901779 3/1989 World Int. Prop. O. .

OTHER PUBLICATIONS

Mulac-Jericevic et al., PNAS, vol. 84, pp. 3633–3637, Jun. 1987.
Ralston et al., Biochemistry, vol. 26, pp. 3261–3266, 1987.
Mulac-Jericevic et al., "Segment alpha 182–198 of Torpedo californica ...," FEBS Lett., vol. 199, No. 1, Apr. 1986, pp. 68–74.
Yokoi et al., "T lymphocyte recognition of acetylcholine receptor: localization ... ," Eur. J. Immunol., vol. 17, 1987, pp. 1697–1702.
Aronheim et al., "Characterization of the binding of alpha-bungarotoxin ... ," J. Biol. Chem., vol. 263, No. 20, Jul. 15, 1988, pp. 9933–9937.
Ralston et al., "Synthetic peptides used to locate the alpha-bungarotoxin ... ," Biochem., vol. 26, 1987, pp. 3261–3266.
Wilson et al., "Binding of alpha-bungarotoxin to synthetic peptides ... ," Biochem., vol. 27, 1988, pp. 6667–6674.
Mulac-Jericevic et al., "alpha-Neurotoxin binding to acetylcholine receptor: localization ... ," Chem. Abs., vol. 108, 1988, pp. 222–223, Ab. No. 33345t. & J. Prot. Chem., 1987, 6(5), 365–73.
Fujii et al., "Specificity of the T cell immune response to acetylcholine ... ," J. Immunol., vol. 140, No. 6, Mar. 1988, pp. 1830–1837.
Nagata, "Immunological studies on myasthenia gravis using synthetic peptides ... ," Chem. Abs., vol. 110, 1989, pp. 625–626, Ab. No. 171542x & Kanazaka Dagaku Juzen Igakkai Zasshi, 1988, 97(3), 704–14.
Radding et al., "alpha-Toxin binding to acetylcholine receptor alpha 179–191 ... ," Chem. Abs., vol. 109, 1988, pp. 200–201, Ab. No. 2071s & FEBS Lett. 1988, 231(1), 212–16.
Noda et al., "Primary structure of alpha-subunit precursor of Torpedo ... ," Nature, vol. 299, 1982, pp. 793–797.

Primary Examiner—Merrell C. Cashion, Jr.
Assistant Examiner—A. M. Davenport
Attorney, Agent, or Firm—Oblon, Spivak, McClelland, Maier & Neustadt

[57] ABSTRACT

There is disclosed an adsorbent, comprising a carrier on which is immobilized a peptide possessing an ability to bind to the human antibody to the nicotinic acetylcholine receptor and represented by the formula:

H—X—A—Y—Z wherein A stands for a peptide residue, one of X and Y stands for a single bond, an amino acid residue selected from the class consisting of Asp, Glu, Lys and a divalent group represented by the formula, $$-\text{NH}(\text{CH}_2)_n\overset{\text{O}}{\underset{\|}{\text{C}}}-$$

(wherein n stands for an integer in the range of 1 to 17), or a peptide residue formed by peptide linkage of two to ten amino acid residues of at least one species selected from the class mentioned above and the other of X and Y stands for an amino acid residue selected from the class consisting of Asp, Glu, Lys and a divalent group represented by the formula, $$-\text{NH}(\text{CH}_2)_n\overset{\text{O}}{\underset{\|}{\text{C}}}-$$

(wherein n stands for an integer in the range of 1 to 17), or a peptide residue formed by peptide linkage of two to ten amino acid residues of at least one species selected from the class mentioned above and Z stands for a hydroxyl group or an amino group. A method for the production of the adsorbent and a method for the use of the adsorbent are also disclosed.

4 Claims, No Drawings

ADSORBENT, METHOD FOR PRODUCTION THEREOF, AND METHOD FOR USE THEREOF

BACKGROUND OF THE INVENTION

1. Field of the Invention

This invention relates to a novel adsorbent, a method for the production thereof, and a method for the use of the adsorbent.

The adsorbent provided by this invention is capable of specifically adsorbing a human antibody to a nicotinic acetylcholine receptor. The adsorbent provided by this invention, therefore, is useful for the therapy of myasthenia gravis which is held to have its main symptoms in the disorder caused in neuromuscular transmission by the autoantibody to the nicotinic acetylcholine receptor present on the post-synaptic membrane in the neuromuscular junctions.

2. Prior Art Statement

It is reported in "Nature", vol. 299, pages 793-797 (1982) that the α-subunit precursor of the nicotinic acetylcholine receptor obtained from the electric organ of *Torpedo californica*, one species of electric ray, is composed of 461 amino acids and that the primary structure of the precursor has been successfully elucidated. According to this report, the amino acid sequence at the 183rd to 200th positions in the primary structure of the α-subunit precursor is represented by the formula: -Gly-Trp-Lys-His-Trp-Val-Tyr-Tyr-Thr-Cys-Cys-Pro-Asp-Thr-Pro-Tyr-Leu-Asp-. In Proceedings of the National Academy of Sciences of the United States of America, Vol. 84, pages 3633-3637 (1987), it is reported that a peptide corresponding to the amino acid sequence at the 182nd to 198th position in the primary structure of the α-subunit of the nicotinic acetylcholine receptor obtained from the electric organ of *Torpedo californica* has been synthesized and that an adsorbent formed by immobilizing this peptide on an agarose type carrier (CNBr-activated Sepharose CL-4B) has an ability to bind itself with a mouse antibody and a rabbit antibody to the nicotinic acetylcholine receptor. In Biochemical and Biophysical Research Communicatons, Vol. 135, pages 82-89 (1986), it is reported that the α-subunit of the nicotinic acetylcholine receptor obtained from *Torpedo californica*, on hydrolysis with a protease, produces a fragment possessing a molecular weight of 18 kilo-daltons and presumed to correspond to the amino acid sequence at the 153rd to 350th positions in the primary structure of the α-subunit and that this fragment has an ability to bind itself with α-bugarotoxin and a mouse monoclonal antibody against the ligand binding site of the nicotinic acetylcholine receptor.

For the therapy of myasthenia gravis it is desired to establish a method for effective removal of the human autoantibody to the nicotinic acetylcholine receptor which is thought to be the main cause of myasthenia gravis.

OBJECT AND SUMMARY OF THE INVENTION

An object of this invention is to provide an efficiently producible and novel adsorbent possessing an ability to adsorb effectively the human antibody to the nicotinic acetylcholine receptor, a method for the production thereof, and a method for the use of the adsorbent.

This invention accomplishes the object mentioned above by providing an adsorbent, comprising a carrier on which is immobilized a peptide possessing an ability to bind to the human antibody to the nicotinic acetylcholine receptor and represented by the formula (I) [hereinafter the peptide will be occasionally referred to as "peptide (I)"]:

$$H-X-A-Y-Z \qquad (I)$$

[wherein A stands for a peptide residue, one of X and Y stands for a single bond, an amino acid residue selected from the class consisting of Asp, Glu, Lys and a divalent group represented by the formula,

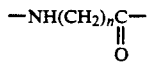

(wherein n stands for an integer in the range of 1 to 17), or a peptide residue formed by peptide linkage of two to ten amino acid residues of at least one species selected from the class mentioned above and the other of X and Y stands for an amino acid residue selected from the class consisting of Asp, Glu, Lys and a divalent group represented by the formula,

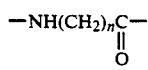

(wherein n stands for an integer in the range of 1 to 17), or a peptide residue formed by peptide linkage of two to ten amino acid residues of at least one species selected from the class mentioned above, and Z stands for one member selected from the class consisting of hydroxyl group and amino group]. The object is also accomplished by this invention providing a method for the production of the adsorbent, which comprises immobilizing the peptide (I) on a carrier. It is further accomplished by this invention by providing a method for the removement of the human antibody to the nicotinic acetylcholine receptor contained in a body fluid, which comprises causing the adsorbent to be in contact with the body fluid.

DETAILED DESCRIPTION OF THE PREFERRED EMBODIMENTS

In this specification, various amino acid residues are denoted by conventional abbreviations. Many abbreviations are well known in the technical field to which the present invention pertains. Those used in this specification are enumerated below.

Asp: L-aspartic acid residue
Cys: L-cysteine acid residue
Glu: L-glutamic acid residue
Gly: Glycine residue
His: L-histidine residue
Leu: L-leucine residue
Lys: L-lysine residue
Pro: L-proline residue
Thr: L-threonine residue
Trp: L-tryptophane residue
Tyr: L-tyrosine residue
Val: L-valine residue Further in this specification, the description of amino acid sequence follows the convention that the amino acid at the N terminal is positioned on the lefthand side and the amino acid at the C terminal on the righthand side.

The peptide (I) can be efficiently immobilized on a carrier. The peptide (I) which is immobilized on a carrier manifests an ability to adsorb the human antibody to the nicotinic acetylcholine receptor in the body fluid such as blood, plasma or serum.

In the general formula (I) representing the peptide (I), the symbol A is defined as set forth above. Examples of the peptide residues represented by A include a peptide residue of the formula:

-Gly-Trp-Lys-His-Trp-Val-Tyr-Tyr-Thr-Cys-Cys-Pro-Asp-Thr-Pro-Tyr-Leu-Asp-     (II)

(wherein two cysteinyl mercapto groups in the Cys-Cys moiety may be interlinked to each other to form a disulfide bond); and one member which is selected from an analog or fragment of the peptide residue of the formula (II) and a fragment of analog of the peptide residue of the formula (II), and which is equivalent in the ability of the peptide of the formula (I) to bind to the human antibody to the nicotinic acetylcholine receptor to the peptide residue of the formula (II).

The symbols X and Y in the general formula (I) have the meanings defined above. Peptides having single bonds for both X and Y and peptides having an amino acid residue or a peptide residue deviating from the respective definition for either of X and Y have the possibility of not merely eluding efficient immobilization on a carrier but also failing to manifest sufficiently an ability to adsorb the human antibody to the nicotinic acetylcholine receptor when they are immobilized on a carrier. The following peptide residues may be mentioned as concrete examples of the peptide residues denoted by the symbols X and Y in the general formula (I).

—Asp—Asp—, —Glu—Glu—, —Lys—Lys—,

—Gly—Gly—, $-\text{NH}(CH_2)_{11}C)_2-$, $-\text{NH}(CH_2)_{17}C)_2-$,
$\qquad\qquad\qquad\qquad\quad \parallel \qquad\qquad\quad\parallel$
$\qquad\qquad\qquad\qquad\quad O \qquad\qquad\quad O$ —Asp—Glu—, —Asp—Gly—, —Glu—Asp—, —Glu—Lys—, —Lys—Glu—, —Lys—NH$(CH_2)_{11}$C—,
$\qquad\qquad\qquad\qquad\qquad\qquad\qquad\qquad\quad \parallel$
$\qquad\qquad\qquad\qquad\qquad\qquad\qquad\qquad\quad O$ —Gly—Asp—, —Gly—Lys—, —NH$(CH_2)_{11}$C—Glu—,
$\qquad\qquad\qquad\qquad\qquad\qquad\qquad\quad \parallel$
$\qquad\qquad\qquad\qquad\qquad\qquad\qquad\quad O$ —NH$(CH_2)_{11}$C—Lys—, —NH$(CH_2)_{17}$C—Asp—,
$\qquad\quad\parallel \qquad\qquad\qquad\qquad\quad\parallel$
$\qquad\quad O \qquad\qquad\qquad\qquad\quad O$ —NH$(CH_2)_{17}$C—Lys—, —Lys—Lys—Gly—,
$\qquad\quad\parallel$
$\qquad\quad O$ $-(\text{Asp})_5-$, $-(\text{Glu})_5-$, $-(\text{Lys})_5-$, $-(\text{Gly})_5-$, $-(\text{NH}(CH_2)_{11}C)_5-$, $-(\text{NH}(CH_2)_{17}C)_5-$,
$\qquad\quad\parallel \qquad\qquad\qquad\quad\parallel$
$\qquad\quad O \qquad\qquad\qquad\quad O$ —Lys—Asp—Glu—Gly—NH$(CH_2)_{17}$C—,
$\qquad\qquad\qquad\qquad\qquad\qquad\quad\parallel$
$\qquad\qquad\qquad\qquad\qquad\qquad\quad O$ —Gly—Lys—Glu—Glu—Asp—, —Asp—Glu—NH$(CH_2)_{17}$C—Lys—Gly—Lys—,
$\qquad\qquad\qquad\qquad\parallel$
$\qquad\qquad\qquad\qquad O$ $-(\text{Asp})_{10}-$, $-(\text{Glu})_{10}-$, $-(\text{Lys})_{10}-$, $-(\text{Gly})_{10}-$, $-(\text{NH}(CH_2)_{11}C)_{10}-$, $-(\text{NH}(CH_2)_{17}C)_{10}-$,
$\qquad\quad\parallel \qquad\qquad\qquad\qquad\parallel$
$\qquad\quad O \qquad\qquad\qquad\qquad O$ —Lys—Glu—Gly—NH$(CH_2)_{11}$C—Asp—Asp—Lys—
$\qquad\qquad\qquad\qquad\qquad\parallel$
$\qquad\qquad\qquad\qquad\qquad O$ Lys—Glu—Gly—, —Lys—Glu—Glu—Gly—Asp—Asp—Lys—Lys—Gly—Gly—.

The carrier on which the peptide (I) is to be immobilized is desired to be of a type possessing a hydrophilic surface, containing a reactive functional group such as amino group, carboxyl group, or hydroxyl group which is available for the formation of a covalent bond with the peptide, exhibiting insolubility in body fluid, and possessing a porous texture. The porous carrier is advantageous in respect that it has a large surface area available for the adsorption of the human antibody to the nicotinic acetylcholine receptor. To be used advantageously, this carrier is desired to possess an exclusive limiting protein molecular weight approximately in the range of $10^6$ to $10^9$ or an average pore diameter approximately in the range of 50 to 1000 nanometers. The carrier can be used in a form freely selected from such forms as particulate form, a fibrous form, a sheet form, and a hollow fiber form. As concrete examples of the carrier, cellulose type carriers represented by CM-cellulofine CH (a product possessing an exclusive limiting protein molecular weight of about $3 \times 10^6$, marketed by Seikagaku Kogyo Co., Ltd.), polyvinyl alcohol type carriers represented by CM-Toyopearl 650C (a product possessing an exclusive limiting protein molecular weight of about $5 \times 10^6$, marketed by Toso K.K., polyacrylamide type carriers represented by CM-Trisacryl M (a product possessing an exclusive limiting protein molecular weight of $1 \times 10^7$, marketed by Pharmacia-LKB, Sweden), agarose type carriers represented by Sepharose CL-4B (a product possessing an exclusive limiting protein molecular weight of $2 \times 10^7$, marketed by Pharmacia-LKB, Sweden), and other similar organic carriers, and porous glass represented by CPG-10-1000 (a product possessing an exclusive limiting molecular weight of $1 \times 10^8$ and an average pore diameter of 100 nm, marketed by Electro-nucleonics Corp., U.S.A.) and other similar inorganic carriers may be cited.

In order for the produced adsorbent to be capable of adsorbing a significant amount of the human antibody to the nicotinic acetylcholine receptor, the amount of the peptide (I) to be immobilized on the carrier of the absorbent according to the invention is generally required to be at least about $3 \times 10-8$ mol/g (carrier). For the peptide of the general formula (I) thus immobilized on the carrier to be effectively utilized for the adsorption of the human antibody, the amount of the peptide to be immobilized is desired to fall approximately in the range of $1 \times 10^7$ to $2 \times 10^{-6}$ mol/g (carrier).

Now, the method for the production of the adsorbent of the present invention will be described below.

The immobilization of the peptide (I) on the carrier is carried out by the method generally employed heretofore in immobilizing peptides and proteins on a carriers. As examples of the such methods, there can be mentioned a method which effects the immobilization by converting the carboxyl group possessed by a carrier through the reaction thereof with N-hydroxysuccinimide into a succinimidoxycarbonyl group and causing the peptide (I) to react in the portion of the amino group thereof with the succinimidoxycarbonyl group (activated ester method), a method which attains the immobilization by allowing the amino group or the carboxyl group possessed by carrier to undergo a condensation reaction with the carboxyl group or the amino group of the peptide (I) in the presence of a condensation reagent such as dicyclohexylcarbodiimide (condensation method), and a method which accomplishes the immobilization by crosslinking a carrier with the peptide (I) by the use of such a compound as glutaraldehyde which possesses at least two functional groups (carrier cross-linking method). The adsorbent which is obtained by immobilizing the peptide (I) on a carrier by the activated ester method possesses the highest ability to adsorb the human antibody to the nicotinic acetylcholine receptor.

The adsorbent contemplated by this invention is produced by immobilizing the peptide (I) on a carrier and optionally heat-treating the peptide (I) as immobilized on the carrier. The peptide (I) thus immobilized on the carrier is enabled by this heat treatment to manifest more conspicuously the high ability thereof to adsorb the human antibody to the nicotinic acetylcholine receptor. This heat treatment is desired to be carried out at a temperature of at least 60° C. If the temperature of the heat treatment is unduly high, there may arise the possibility that the peptide (I) and/or the carrier will be decomposed. Thus, it is desired to be kept from exceeding 180° C. The time of this heat treatment is desired to be at least about 5 minutes. If this time is unduly long, there is a possibility that the peptide (I) and/or the carrier will be decomposed. Thus, it is desired not to exceed about one hour. Optionally, the heat treatment can be executed by heating the peptide (I) immobilized on the carrier in water or an aqueous solution under the conditions specified above. For the sake of curbing the otherwise possible decomposition of the peptide (I), the heat treatment is desired to be carried out in a buffer solution such as a sodium chloride-containing phosphate buffer.

The synthesis of a peptide (I) can be accomplished by the method generally employed heretofore for the synthesis of peptides. As examples of such conventional methods, the solid-phase synthesis method and such liquid-phase synthesis methods as the stepwise elongation method and the fragment condensation method may be mentioned. From the operational point of view, it is convenient to effect the synthesis by the solid-phase synthesis method [as reported in Journal of the American Chemical Society, vol. 85, pages 2149–2154 (1963)].

Now, the synthesis of a peptide (I) in accordance with the solid-phase synthesis method will be described below. This synthesis is accomplished by sequentially repeating an operation of binding through condensation to such a polymer insoluble in a reaction solvent as a styrene-divinylbenzene copolymer having bonded thereto an acyloxy group or an acylamino group obtained by removing a hydrogen atom respectively from an α-carboxyl group or an α-cabamoyl group possessed by an amino acid or an amino acid amide corresponding to the C terminal of the peptide (I) aimed at the corresponding component amino acids in the order of their occurrence in the direction of the N terminal of the peptide, with such a functional group as α-amino group other than the α-carboxyl group possessed by the relevant amino acid kept in a protected form, and an operation of removing a protective group from the amino group to be caused to form the peptide bond, such as α-amino group, which group is possessed by the bound amino acid, thereby attaining gradual growth of a peptide chain and eventually completing a peptide chain corresponding to the peptide aimed at, and separating the peptide chain from the polymer and, at the same time, removing the protecting groups from the protected functional groups and consequently obtaining the peptide, and finally purifying the peptide. In this case, for the sake of precluding otherwise possible occurrence of side reactions, the separation of the peptide chain from the polymer and the removal of the protecting groups are desired to be simultaneously effected by the use of hydrogen fluoride. The purification of the peptide (I) so obtained can be effectively attained by reverse-phase liquid chromatography.

The movement of the human antibody to the nicotinic acetylcholine receptor by the use of the adsorbent according to the present invention is effected by causing the adsorbent to be in contact with a body fluid, such as blood, plasma, or serum, containing said antibody thereby effecting adsorption of the antibody on the adsorbent. For instance, the adsorbent according to the present invention is packed in a column for use. The column used for this purpose should preferably be provided with an inlet and an outlet designed to allow easy connection with the blood circuit, and with a filter made of, for example, polyester and set between the inlet and the adsorbent layer, and between the outlet and the adsorbent layer. The column may be made of polyethylene, polypropylene, polycarbonate, polystyrene or polymethyl methacrylate. Of these polypropylene and polycarbonate are preferred materials, because the column packed with the adsorbent is sterilized (e.g. autoclave or α-ray sterilization) before use.

The human antibody to the nicotinic acetylcholine receptor can be removed from the body fluid of patients by the extracorporeal blood circulation system using a packed column as described above. The following two types of extracorporeal blood circulation system may be mentioned.

(1) Blood taken from a blood vessel of a patient is forced to pass through a column packed with the adsorbent of this invention to remove from it by adsorption the human antibody to the nicotinic acetylcholine receptor, and the clarified blood from the column is returned to the blood vessel of the patient.

(2) Blood taken from a blood vessel of a patient is first separated into haemocytes and plasma, the plasma thus separated is then forced to pass through a column packed with the adsorbent of this invention to remove from it by adsorption the human antibody to the nicotinic acetylcholine receptor, the clarified plasma from the column is mixed with the haemocytes separated above, and the mixture is returned to the blood vessel of the patient.

Now, the present invention will be described specifically below with reference to working examples. It should be noted, however, that this invention is not restricted by these examples.

SYNTHESIZING EXAMPLE 1

A peptide represented by the formula, H-Lys-Lys-Gly-Trp-Lys-His-Trp-Val-Tyr-Tyr-Thr-Cys-Cys-Pro-Asp-Thr-Prq-Tyr-Leu-Asp-Lys-Lys-Gly-OH, was synthesized by the solid-phase synthesis method using an automatic peptide synthesizing apparatus (produced by Applied Biosystems Inc., U.S.A. and marketed as "Model 430A"). In accordance with the series of operations indicated in Table 1, the amino acids selected from among L-aspartic acid, L-cysteine, glycine, L-histidine, L-leucine, L-lysine, L-proline, L-threonine, L-tryptophane, L-thyrosine, and L-valine corresponding to the component amino acids of the peptide in the order of occurrence in the direction of the N terminal of the peptide were sequentially bound to 0.64 g of a particulate resin of a styrene-divinylbenzene copolymer (the molar ratio of styrene to divinylbenzene 99 : 1) possessing a 4-[N-(t-butoxycarbonyl)glycyloxymethyl]phenylacetamidomethyl group,

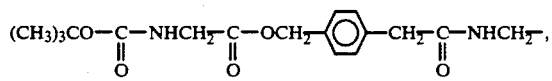

a ratio of 0.78 mmol/g (resin) (produced by Applied Biosystems Inc., U.S.A. and marketed under the tradename "PAM Glycine, t-Boc-Gly"). In the condensation reaction, the amino acids mentioned above were used respectively in the form of N-(t-butoxycarbonyl)-$O^4$-benzyl-L-aspartic anhydride, N-(t-butoxycarbonyl)-S-(p-methoxybenzyl)-L-cysteine anhydride, N-(t-butoxycarbonyl)glycine anhydride, $N^{60}$-(t-butoxycarbonyl)-$N^{Im}$-tosyl-L-histidine anhydride, N-(t-butoxycarbonyl)-L-leucine anhydride, $N^2$-(t-butoxycarbonyl)-$N^6$-benzyloxycarbonyl-L-lysine anhydride, N-(t-butoxycarbonyl)-L-proline anhydride, N-(t-butoxycarbonyl)-L-triptophane anhydride, N-(t-butoxycarbonyl)-$O^4$-benzyl-L-thyrosine anhydride, and N-(t-butoxycarbonyl)-L-valine anhydride each in an amount of about 2 mols per mol of the substrate. The condensation reaction was carried out at normal room temperature. The reaction time was varied with the kind of amino acid to be condensed within the range of 18 to 30 minutes. Since the particular condensation reaction using the $N^2$-(t-butoxycarbonyl)-$N^{Im}$-tosyl-L-histidine anhydride did not show sufficient conversion, it was carried out a second time by repeating the steps 4 to 6 indicated in Table 1 after the series of operation indicated in Table 1 had been completed.

TABLE 1

| Step | Solvent and/or reagent used | Time (min.) | Number of rounds |
|---|---|---|---|
| 1 Removal of t-butoxycarbonyl group | Dichloromethane solution containing 33% by volume of trifluoroacetic acid (10 to 23 ml) | 1.3 | 1 |
| | Dichloromethane solution containing 50% by volume of trifluoroacetic acid (6 to 16 ml) | 18.5 | 1 |
| 2 Washing | Dichloromethane | 1 | 3 |
| 3 Neutralization | Dimethylformamide solution containing 10% by volume of diisopropylethylamine | 1 | 2 |
| 4 Washing | Dimethylformamide | 1 | 5 |
| 5 Condensation reaction | Dimethylformamide solution containing amino acid (10 to 25 ml) | 18 to 30 | 1 |
| 6 Washing | Dichloromethane | 1 | 5 |

The resin obtained after completion of the reactional operation on all the amino acids was washed on a glass filter sequentially with diethyl ether, dichloromehane, and methanol and then vacuum dried. Consequently there was obtained 2.1 g of dry resin. In a reaction vessel made of polytrifluoromonochloroethylene (produced by Peptide Kenkyusho K.K. and marketed as "HF-Reaction Apparatus, Model I"), 1 g of the dry resin was mixed with 1.5 ml of anisole and 0.25 ml of ethyl methyl sulfide and the resultant mixture and 10 ml of hydrogen fluoride added thereto at a temperature of −20° C. were stirred for 30 minutes at the same temperature and for another 30 minutes at a temperature of 0° C. The resultant reaction mixture was evaporated under a vacuum to remove hydrogen fluoride, anisole, and ethyl methyl sulfide. The residue of the evaporation was thoroughly washed with diethyl ether on a glass filter. The residue of the washing was extracted with 2N aqueous acetic acid solution. When the extract was freeze-dried, there was obtained 0.5 g of crude peptide.

When this crude peptide was purified by fractionating reverse-phase high-speed liquid chromatography [column—a column packed with octadecylated silica gel possessing a particle diameter of 5 μm (produced by Chemco K.K. and marketed under the tradename "Develosil ODS 10 mm $\phi \times 300$ mm"); mobile phase—a mixed solvent of acetonitrile and water (with the concentration of acetonitrile gradually varied from 20 vol % to 35 vol % over a period of 20 minutes) containing 0.05% by volume of trifluoroacetic acid], there was obtained 50 mg of the purified peptide aimed at.

When the purified peptide was subjected to analyzing reverse-phase high-speed liquid chromatography [column—a column packed with octadecylated silica gel possessing a particle diameter of 5 μm (produced by Toso K.K. and marketed as "TSK gel ODS-80TM 4 mm $\phi \times 150$ mm"); mobile phase—a mixed solvent of acetonitrile and water (with the concentration of acetonitrile gradually varied from 5 vol % to 50 vol % over a period of 30 minutes) containing 0.05% by volume of trifluoroacetic acid; flow rate—1 ml/min.; method of detection—absorbancy at a wavelength of 210 nm], a single sharp peak was observed at 19.2 min. By FAB (fast atomic bombardment) mass spectrometry, the purified peptide was found to possess a molecular weight of 2,814 (theoretical value 2,815.21). This purified peptide was hydrolyzed with hydrochloric acid and the resultant hydrolyzate was analyzed for amino acid composition. The results of this analysis were as shown below: (The parenthesized numerals indicate theoretical values.) Lysine—5.23 (5), glycine—1.94 (2), tryptophane—2.02 (2), histidine—0.98 (1), valine —0.92 (1), thyrosine—3.07 (3), threonine—2.07 (2), cystine—0.85 (1), proline—2.13 (2), aspartic acid—2.10 (2), and leucine—1.00 (1).

SYNTHESIZING EXAMPLES 2 TO 16

The peptides indicated in Table 2 were obtained by carrying out solid-phase synthesis of peptide and purification in the same manner as in Synthesizing Example 1. As solid-phase resins, a particulate resin of a styrene-divinylbenzene copolymer (the molar ratio of styrene to divinylbenzene 99 : 1) possessing a 4-[N-(t-butoxycarbonyl)glycyloxymethyl]phenylacetamidomethyl group in a ratio of 0.78 mmol/g (resin) (produced by Applied Biosystems Inc., U.S.A. and marketed under the tradename "PAM Glycine,t-Boc-Gly") was used in Synthesizing Example 2 and Synthesizing Example 10; a particulate resin of a styrene-divinylbenzene copolymer (the molar ratio of styrene to divinylbenzene 99 : 1)

possessing a 4-[N-(t-butoxycarbonyl)-O$^4$-benzyl-α-L-aspartyloxymethyl]phenylacetamidomethyl group in a ratio of 0.78 mmol/g (resin) [produced by Applied Biosystems Inc., U.S.A. and marketed under the tradename "PAM Aspartic Acid,t-Boc-L-Asp (OBzl)] in Synthesizing Example 3, Synthesizing Example 5, Synthesizing Example 8 and Synthesizing Example 12; a particulate resin of a styrenedivinyl-benzene copolymer (the molar ratio of styrene to divinylbenzene 99 : 1) possessing a 4-[N-(t-butoxycarbonyl)-O$^5$-benzyl-α-L-glutamyloxymethyl]phenylacetamidomethyl group in a ratio of 0.78 mmol/g (resin) [produced by Applied Biosystems Inc., U.S.A. and marketed under the tradename "PAM Glutamic Acid,t-Boc-L-Glu(OBzl)"] in Synthesizing Example 4 and Synthesizing Example 6; a particulate resin of a styrene-divinylbenzene copolymer (the molar ratio of styrene to divinylbenzene 99 : 1) possessing a 4-[N$^2$-(t-butoxycarbonyl)-N$^6$-(chlorobenzyloxycarbonyl)-L-lysyloxymethyl]-phenylacetamidomethyl group in a ratio of 0.78 mmol/g (resin) [produced by Applied Biosystems Inc., U.S.A. and marketed under the tradename "PAM Lysine,t-Boc-L-Lys (ClZ)"] in Synthesizing Example 7, Synthesizing Example 9 and Synthesizing Example 11; and a particulate resin of a styrene-divinylbenzene copolymer (the molar ratio of styrene to divinylbenzene 99 : 1) possessing an α-amino-p-methylbenzyl group in a ratio of 0.78 mmol/g (resin) (produced by Applied Biosystems Inc., U.S.A. and marketed under the tradename "p-Methyl BHA Resin") in Synthesizing Examples 13 to 16. In the condensation reaction, L-glutamic acid, 12-aminododecanoic acid, and 18-aminooctadecanoic acid were used respectively in the form of N-(t-butoxycarbonyl)-O$^5$-benzyl-L-glutamic anhydride, 12-(t-butoxycarbonylamino)dodecanoic anhydride, and 18-(t-butoxycarbonylamino)octadecanoic anhydride.

In analyzing reverse-phase high-speed liquid chromatography, the produced peptides each showed a single peak. The molecular weights of the purified peptides determined by FAB mass spectrometry and the amino acid composition analyses of the products obtained by hydrolyzing the purified peptides with hydrochloric acid were as shown in Table 3.

TABLE 2

| Synthesizing Example | Peptide represented by the general formula (I) (Note 1) | | |
|---|---|---|---|
| | X | Y | Z |
| 2 | — | Gly | OH |
| 3 | —NH(CH$_2$)$_{17}$CO— | — | OH |
| 4 | —NH(CH$_2$)$_{11}$CO— | -(Glu)$_5$ | OH |
| 5 | -(Lys)$_5$ | -(Asp)$_5$ | OH |
| 6 | -(Lys)$_{10}$ | Glu | OH |
| 7 | -(Gly)$_5$ | —Gly—Lys— | OH |
| 8 | —Lys—Asp—Glu—Gly—NH(CH$_2$)$_{17}$CO— | Asp | OH |
| 9 | Gly | —Lys—Lys— | OH |
| 10 | Asp | —Lys—Glu—Gly—NH(CH$_2$)$_{11}$CO—Asp—Asp—Lys—Lys—Glu—Gly— | OH |
| 11 | Glu | —Asp—Glu—NH(CH$_2$)$_{17}$CO—Lys—Gly—Lys— | OH |
| 12 | —Lys—Glu—Glu—Gly—Asp—Asp—Lys—Lys—Gly—Gly— | —Gly—Lys—Glu—Glu—Asp— | OH |
| 13 | Lys | —NH(CH$_2$)$_{17}$CO— | NH$_2$ |
| 14 | —Lys—Lys— | —Asp—Gly— | NH$_2$ |
| 15 | -(Glu)$_{10}$ | Lys | NH$_2$ |
| 16 | —NH(CH$_2$)$_{11}$CO— | —NH(CH$_2$)$_{11}$CO— | NH$_2$ |

(Note 1)
A in the formula (I) shows the peptide residue represented by the formula —Gly—Trp—Lys—His—Trp—Val—Tyr—Tyr—Thr—Cys—Cys—
Pro—Asp—Thr—Pro—Tyr—Leu—Asp—.

TABLE 3 - (1)

| | Synthesizing Example No. | | | | | | | |
|---|---|---|---|---|---|---|---|---|
| | 2 | 3 | 4 | 5 | 6 | 7 | 8 | 9 |
| | Molecular weight determined by FAB mass spectrometry | | | | | | | |
| Amino acid composition analyses | 2303 (2302.52) | 2527 (2526.93) | 3088 (3088.343) | 3462 (3461.77) | 3656 (3656.30) | 2716 (2715.95) | 3071 (3071.447) | 2559 (2558.863) |
| Glycine | 1.92 (2) | 0.92 (1) | 0.94 (1) | 0.95 (1) | 0.97 (1) | 6.90 (7) | 1.92 (2) | 1.94 (2) |
| Tryptophane | 2.01 (2) | 2.03 (2) | 2.05 (2) | 2.02 (2) | 2.04 (2) | 2.03 (2) | 2.01 (2) | 2.02 (2) |
| Lysine | 1.03 (1) | 1.05 (1) | 1.06 (1) | 6.18 (6) | 11.21 (11) | 2.08 (2) | 2.03 (2) | 3.05 (3) |
| Histidine | 0.99 (1) | 0.97 (1) | 0.96 (1) | 0.97 (1) | 0.97 (1) | 0.95 (1) | 0.99 (1) | 0.98 (1) |
| Valine | 0.94 (1) | 0.96 (1) | 0.97 (1) | 0.95 (1) | 0.97 (1) | 0.96 (1) | 0.95 (1) | 0.96 (1) |
| Thyrosine | 3.10 (3) | 3.14 (3) | 3.14 (3) | 3.10 (3) | 3.09 (3) | 3.12 (3) | 3.10 (3) | 3.11 (3) |
| Threonine | 2.06 (2) | 2.04 (2) | 2.05 (2) | 2.03 (2) | 2.04 (2) | 2.04 (2) | 2.06 (2) | 2.05 (2) |
| Cystine | 0.87 (1) | 0.86 (1) | 0.84 (1) | 0.85 (1) | 0.87 (1) | 0.85 (1) | 0.86 (1) | 0.87 (1) |
| Proline | 2.09 (2) | 2.06 (2) | 2.05 (2) | 2.07 (2) | 2.09 (2) | 2.08 (2) | 2.09 (2) | 2.10 (2) |
| Aspartic acid | 2.14 (2) | 2.10 (2) | 2.12 (2) | 7.35 (7) | 2.10 (2) | 2.12 (2) | 4.13 (4) | 2.11 (2) |
| Leucine | 0.99 (1) | 1.01 (1) | 1.00 (1) | 1.01 (1) | 1.00 (1) | 0.98 (1) | 0.99 (1) | 1.00 (1) |
| Glutamic acid | — | — | 5.15 (5) | — | 1.02 (1) | — | 1.01 (1) | — |
| H$_2$N(CH$_2$)$_{11}$COOH | — | — | 0.96 (1) | — | — | — | — | — |
| H$_2$N(CH$_2$)$_{17}$COOH | — | 0.94 (1) | — | — | — | — | 0.95 (1) | — |

| | Synthesizing Example No. | | | | | | |
|---|---|---|---|---|---|---|---|
| | 10 | 11 | 12 | 13 | 14 | 15 | 16 |

TABLE 3 - (1)-continued

| Amino acid composition analyses | Molecular weight determined by FAB mass spectrometry | | | | | | |
|---|---|---|---|---|---|---|---|
| | 3488 (3487.833) | 3214 (3213.645) | 3920 (3920.145) | 2654 (2654.121) | 2558 (2557.88) | 3664 (3663.80) | 2639 (2639.10) |
| Glycine | 2.91 (3) | 1.98 (2) | 4.92 (5) | 0.96 (1) | 1.93 (2) | 0.96 (1) | 0.95 (1) |
| Tryptophane | 2.02 (2) | 2.03 (2) | 2.01 (2) | 2.02 (2) | 2.02 (2) | 2.01 (2) | 2 03 (2) |
| Lysine | 5.10 (5) | 3.06 (3) | 5.12 (5) | 2.04 (2) | 3.09 (3) | 2.06 (2) | 1.03 (1) |
| Histidine | 0.98 (1) | 0.99 (1) | 0.97 (1) | 0.99 (1) | 0.96 (1) | 0.98 (1) | 0.99 (1) |
| Valine | 0.95 (1) | 0.96 (1) | 0.94 (1) | 0.95 (1) | 0.95 (1) | 0.95 (1) | 0.94 (1) |
| Thyrosine | 3.10 (3) | 3.09 (3) | 3.07 (3) | 3.07 (3) | 3.10 (3) | 3.08 (3) | 3.11 (3) |
| Threonine | 2.04 (2) | 2.05 (2) | 2.06 (2) | 2.05 (2) | 2.06 (2) | 2.05 (2) | 2.07 (2) |
| Cystine | 0.90 (1) | 0.88 (1) | 0.89 (1) | 0.87 (1) | 0.86 (1) | 0.85 (1) | 0.87 (1) |
| Proline | 2.08 (2) | 2.09 (2) | 2.08 (2) | 2.07 (2) | 2.10 (2) | 2.07 (2) | 2.09 (2) |
| Aspartic acid | 5.25 (5) | 3.09 (3) | 5.18 (5) | 2.12 (2) | 3.15 (3) | 2.15 (2) | 2.14 (2) |
| Leucine | 0.98 (1) | 0.99 (1) | 1.00 (1) | 0.99 (1) | 0.99 (1) | 1.01 (1) | 1.00 (1) |
| Glutamic acid | 2.04 (2) | 2.03 (2) | 4.07 (4) | — | — | 10.50 (10) | — |
| $H_2N(CH_2)_{11}COOH$ | 0.94 (1) | — | — | — | — | — | 1.94 (2) |
| $H_2N(CH_2)_{17}COOH$ | — | 0.95 (1) | — | 0.94 (1) | — | — | — |

(Note)
The parenthesized numerals indicate theoretical values.

SYNTHESIZING EXAMPLES 17 AND 18

A peptide represented by the formula, H-Gly-Trp-Lys-His-Trp-Val-Tyr-Tyr-Thr

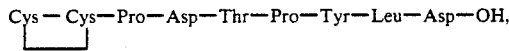

Cys — Cys—Pro—Asp—Thr—Pro—Tyr—Leu—Asp—OH, (Synthesizing Example 17) and a peptide represented by the formula,

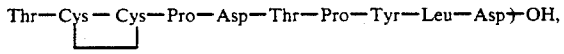

Thr—Cys — Cys—Pro—Asp—Thr—Pro—Tyr—Leu—Asp)—OH, (Synthesizing Example 18) were obtained by carrying out solid-phase synthesis and purification of peptide in the same manner as in Synthesizing Example 1. As a solid-phase resin, a particulate resin of a styrenedivinylbenzene copolymer (molar ratio of styrene to divinylbenzene 99 : 1) possessing a 4-[N-(t-butoxycarbonyl)-O⁴-benzyl-α-L-aspartyloxymethyl]-phenylacetoamidomethyl group in a ratio of 0.78 mmol/g (resin) [produced by Applied Biosystems Inc., U.S.A. and marketed under the tradename "PAM Aspartic Acid,t-Boc-L-Asp(OBzl)"] was used.

By analyzing reverse-phase high-speed liquid chromatography, the purified peptides consequently obtained each showed a single peak. The molecular weights of the purified peptides determined by FAB mass spectrometry and the amino acid composition analyses of the products obtained by hydrolyzing the purified peptides with hydrochloric acid were as shown in Table 4.

TABLE 4

| | Synthesizing Example 17 | Synthesizing Example 18 |
|---|---|---|
| | Molecular weight determined by FAB mass spectrometry | |
| Amino acid composition analyses | 2245 (2245.467) | 2472 (2471.78) |
| Glycine | 0.96 (1) | 0.97 (1) |
| Tryptophane | 2.02 (2) | 2.01 (2) |
| Lysine | 1.02 (1) | 1.02 (1) |
| Histidine | 0.97 (1) | 0.98 (1) |
| Valine | 0.95 (1) | 0.94 (1) |

TABLE 4-continued

| | Synthesizing Example 17 | Synthesizing Example 18 |
|---|---|---|
| | Molecular weight determined by FAB mass spectrometry | |
| Amino acid composition analyses | 2245 (2245.467) | 2472 (2471.78) |
| Thyrosine | 3.12 (3) | 3.11 (3) |
| Threonine | 2.07 (2) | 2.06 (2) |
| Cystine | 0.86 (1) | 0.87 (1) |
| Proline | 2.08 (2) | 2.07 (2) |
| Aspartic acid | 2.12 (2) | 2.15 (2) |
| Leucine | 0.99 (1) | 2.98 (3) |

(Note)
The parenthesized numerals indicate theoretical values.

EXAMPLE 1

(a) In 50 ml of dioxane obtained by distillation in the presence of sodium metal, 10 g of cellulose particles (marketed by Seikagaku Kogyo Co., Ltd. under the tradename "CM-Cellulofine CH") were suspended. In the suspension, 0.5 g of N-hydroxysuccinimide and 1.0 g of dicyclohexylcarbodiimide added thereto were shaken overnight at room temperature. The resultant mixture was washed with a phosphate buffer solution (0.02 mol/liter) of pH 7.4 and suction filtered. The particles consequently obtained and 20 ml of a phosphate buffer solution (0.02 mol/liter) of pH 7.4 containing 20 mg of the peptide of Synthesizing Example 1 added thereto were stirred overnight at a temperature of 4° C. The mixture consequently obtained was suction filtered. By analyzing reverse-phase high-speed liquid chromatography, the filtrate was found to contain no peptide (immobilization ratio of peptide on carrier: about 100%). Thus, about 10 g of cellulose particles (the adsorbent not heat treated) having immobilized thereon 20 mg of the peptide of Synthesizing Example 1 were obtained.

(b) In 5 ml aliquots of a phosphate buffer solution (0.02 mol/liter) of pH 7.4 containing sodium chloride in a concentration of 0.15 mol/liter, the peptide-immobilized cellulose particles obtained as described above were suspended in a unit amount of 1 g. The resultant suspension were heat treated at various temperatures, i.e. 80° C. (over a water bath under normal atmospheric pressure), 100° C. (over a water bath under normal atmospheric pressure), 121° C. (in an autoclave under application of pressure), 150° C. (in an autoclave under application of pressure), for 20 minutes. Thus, heat-treated adsorbents were obtained.

EXAMPLE 2

(a) About 10 g of polyvinyl alcohol particles (adsorbent subjected to no heat treatment) having immobilized thereon 18.4 mg of the peptide obtained in Synthesizing Example 2 (ratio of peptide immobilization: about 92%) were obtained by following the procedure of Example 1(a), except that 10 g of polyvinyl alcohol particles (produced by Toso K.K. and marketed under the tradename "CM-Toyopearl650C") were used in place of 10 g of the cellulose particles and 20 mg of the peptide obtained in Synthesizing Example 2 was used in place of 20 mg of the peptide obtained in Synthesizing Example 1.

(b) In 5 ml of a phosphate buffer solution (0.02 mol/liter) of pH 7.4 containing sodium chloride in a concentration of 0.15 mol/liter, 1 g of the peptide-immobilized polyvinyl alcohol particles obtained as described above were suspended. The resultant suspension was heat treated in an autoclave under application of pressure at a temperature of 121° C. for 20 minutes. Thus, a heat-treated adsorbent was obtained.

EXAMPLE 3

(a) In 100 ml of toluene solution containing 5 ml of α-aminopropyl triethoxy silane, 10 g of porous glass particles (produced by Electro-nucleonics Crop., U.S.A. and marketed as "CPG-10-1000") were reacted under reflux for 24 hours. The resultant mixture was washed with dioxane obtained by distillation in the presence of sodium metal and the washed mixture was suction filtered. The particles consequently obtained were suspended in 100 ml of dioxide obtained by distillation in the presence of sodium metal. The resultant suspension and 3 g of succinic anhydride added thereto were stirred overnight at normal room temperature. The resultant mixture was washed with dioxane obtained by distillation in the presence of sodium metal and the washed mixture was suction filtered. The particles consequently obtained were suspended in 50 ml of dioxane obtained by distillation in the presence of sodium metal. The resultant suspension and 0.5 g of N-hydroxysuccinimide and 1.0 g of dicyclohexyl-carbodiimide added thereto were stirred overnight at normal room temperature. The resultant mixture was washed with a phosphate buffer solution (0.02 mol/liter) of pH 7.4 and the washed mixture was suction filtered. The particles consequently obtained and 20 ml of a phosphate buffer solution (0.02 mol/liter) of pH 7.4 containing 20 mg of the peptide of Synthesizing Example 3 added thereto were stirred overnight at a temperature of 4° C. The resultant mixture was suction filtered. As a result, about 10 g of porous glass particles (the adsorbent not heat treated) having immobilized thereon 20 mg of the peptide of Synthesizing Example 3 were obtained (ratio of peptide immobilization: about 100%).

(b) A heat-treated adsorbent was obtained by following the procedure of Example 2 (b), expect that 1 g of the peptide-immobilized porous glass particles obtained as described above were used in place of 1 g of the peptide-immobilized polyvinyl alcohol particles.

EXAMPLES 4 TO 16

(a) Peptide-immobilized particulate carriers (the adsorbent not heat treated) were obtained by following the procedures of Example 1(a), Example 2(a) and Example 3(a), except that 20 mg of various peptides indicated in Table 5 were used instead. The particulate carriers and the ratios of peptide immobilization on such carriers were as shown in Table 5.

(b) Heat-treated adsorbents were obtained by following the procedure of Example 2(b), except that the peptide-immobilized particulate carriers obtained as described above were used each in a unit amount ob 1 g in place of 1 g of the peptide-immobilized polyvinyl alcohol particles obtained in Example 2(a).

TABLE 5

| Example | Peptide | Particulate carrier (Note) | Ratio of immobilization |
| --- | --- | --- | --- |
| 4 | Product of Synthesizing Example 4 | Cellulose | About 100 |
| 5 | Product of Synthesizing Example 5 | Cellulose | About 98 |
| 6 | Product of Synthesizing Example 6 | Cellulose | About 100 |
| 7 | Product of Synthesizing Example 7 | Polyvinyl alcohol | About 95 |
| 8 | Product of Synthesizing Example 8 | Polyvinyl alcohol | About 95 |
| 9 | Product of Synthesizing Example 9 | Cellulose | About 95 |
| 10 | Product of Synthesizing Example 10 | Cellulose | About 98 |
| 11 | Product of Synthesizing Example 11 | Cellulose | About 100 |
| 12 | Product of Synthesizing Example 12 | Cellulose | About 100 |
| 13 | Product of Synthesizing Example 13 | Polyvinyl alcohol | About 90 |
| 14 | Product of Synthesizing Example 14 | Polyvinyl alcohol | About 100 |
| 15 | Product of Synthesizing Example 15 | Porous glass | About 95 |
| 16 | Product of Synthesizing Example 16 | Porous glass | About 100 |

(Note)
Cellulose particles: Marketed by Seikagaku Kogyo Co., Ltd. under the tradename "CM-Cellulofine CH"
Polyvinyl alcohol particles: Produced by Toso K.K. and marketed under the tradename "CM-Toyopearl 650C"
Porous glass particles: Produced by Electro-nucelonics Corp., U.S.A. and marketed as "CPG-10-1000"

COMPARATIVE EXAMPLE 1

(a) About 10 g of cellulose particles having immobilized thereon 14.4 mg of the peptide obtained in Synthesizing Example 17 (ratio of peptide immobilization: about 72%) were obtained by following the procedure of Example 1(a), except that 20 mg of the peptide obtained in Synthesizing Example 17 was used in place of 20 mg of the peptide obtained in Synthesizing Example 1.

(b) A heat-treated adsorbent was obtained by following the procedure of Example 2(b), except that 1 g of the peptide-immobilized cellulose particles obtained as described above were used in place of 1 g of the peptide-immobilized polyvinyl alcohol particles.

COMPARATIVE EXAMPLE 2

(a) The immobilization procedure of Example 2(a) was repeated, except that 20 mg of the peptide obtained in Synthesizing Example 18 was used in place of 20 mg of the peptide obtained in Synthesizing Example 2. Since the peptide obtained in Synthesizing Example 18 showed low solubility in the phosphate buffer solution, the peptide remaining in the filtrate could not be determined by analyzing reverse-phase high-speed liquid chromatography.

(b) A heat-treated absorbent was obtained by following the procedure of Example 2(b), expect that 1 g of the polyvinyl alcohol particles obtained by the immobilization treatment described above were used in place of 1 g of the peptide-immobilized polyvinyl alcohol particles obtained in Example 2(a).

TEST EXAMPLE 1

In 0.5 ml of serum from a patient of myasthenia gravis, 50 mg of the adsorbent obtained in Example 1 subjected to no heat treatment or subjected to a heat treatment was suspended at a temperature of 37° C. for three hours. The resultant suspension was centrifuged to separate a supernatant. The supernatant was tested for the concentration of the human antibody to the nicotinic acetylcholine receptor by the Con A method [Protein Nucelic Acid and Enzyme, vol. 26, pages 1578–1591 (1981)]. To be specific, the specimen was brought into contact sequentially with the nicotinic acetylcholine receptor and a radioisotope-labelled α-bungarotoxin. The treated specimen was passed through a column packed with Sepharose having immobilized thereon concanavalin A (Con A). By measuring the radioactivity of the column, the amount of the human antibody which was contained in the specimen and which inhibited the binding of the α-bungarotoxin with the nicotinic acetylcholine receptor was determined in terms of toxin binding inhibition activity (ratio of decrease of the radioactivity of the column). The results are shown in Table 6. For comparison, the results obtained for the glycine-immobilized cellulose particles produced by following the procedure of Example 1(a), except that glycine was used in place of the peptide of Synthesizing Example 1, and the results obtained for the adsorbent produced by a heat treatment at 121° C. in the same manner as in Example 1(b), except that the glycine-immobilized cellulose particles were used in place of the peptide-immobilized cellulose particles, are shown in the same table.

TABLE 6

| Substance immobilized on cellulose particles | Temperature of heat treatment (°C.) | Toxine binding inhibition activity (%) |
|---|---|---|
| Peptide obtained in Synthesizing Example 1 | No heat treatment | 38 |
| Peptide obtained in Synthesizing Example 1 | 80 | 30 |
| Peptide obtained in Synthesizing Example 1 | 100 | 28 |
| Peptide obtained in Synthesizing Example 1 | 121 | 26 |
| Peptide obtained in Synthesizing Example 1 | 150 | 27 |
| Glycine | No heat treatment | 44 |
| Glycine | 121 | 45 |

TEST EXAMPLE 2

Suspension of serum was carried out by following the procedure of Test Example 1, except that various adsorbents obtained in Examples 2 to 16 subjected to a heat treatment was used in place of the adsorbent obtained in Example 1, already subjected to a heat treatment or subjected to no treatment. The supernatant consequently obtained was tested for the concentration of the human antibody to the nicotinic acetylcholine receptor. The results are shown in Table 7. For comparison, the results obtained for the adsorbents of Comparative Example 1 and Comparative Example 2 invariably subjected to a heat treatment and the results obtained for the adsorbent produced by heat-treating at 121° C. the glycine-immobilized cellulose particles as used for comparison in Test Example 1 are shown in Table 7.

TABLE 7

| Adsorbent | Toxin binding inhibition activity (%) |
|---|---|
| Product of Example 2 | 22 |
| Product of Example 3 | 19 |
| Product of Example 4 | 17 |
| Product of Example 5 | 18 |
| Product of Example 6 | 18 |
| Product of Example 7 | 21 |
| Product of Example 8 | 20 |
| Product of Example 9 | 18 |
| Product of Example 10 | 19 |
| Product of Example 11 | 22 |
| Product of Example 12 | 20 |
| Product of Example 13 | 22 |
| Product of Example 14 | 17 |
| Product of Example 15 | 20 |
| Product of Example 16 | 18 |
| Product of Comparative Example 1 | 28 |
| Product of Comparative Example 2 | 36 |
| Product obtained by heat-treating glycine-immobilized cellulose particles at 121° C. | 34 |

As demonstrated in the working examples cited above, this invention provides a normal absorbent capable of effectively adsorbing the human antibody to the nicotinic acetylcholine receptor.

The adsorbent is efficiently produced by using the peptide (I). Further, the human antibody to the nicotinic acetylcholine receptor can be removed by the use of the adsorbent.

What is claimed is:

1. An adsorbent, comprising a carrier on which is immobilized a peptide possessing an ability to bind to the human antibody to the nicotinic acetylcholine receptor and represented by the formula:

H-X-Gly-Trp-Lys-His-Trp-Val-Tyr-Tyr-Thr-Cys-Cys-Pro-Asp-Thr-Pro-Tyr-Leu-Asp-Y-Z wherein one of X and Y stands for a single bond, an amino acid residue selected from the class consisting of Asp, Glu, Lys and a divalent group represented by the formula:

$$-NH(CH_2)_n\underset{O}{\overset{\|}{C}}-$$

(wherein n stands for an integer in the range of 1 to 17), or a peptide residue formed by peptide linkage of two to ten amino acid residues of at least one species selected from the class mentioned above and the other of X and Y stands for an amino acid residue selected from the class consisting of Asp, Glu, Lys and a divalent group represented by the formula, $$-\text{NH}(\text{CH}_2)_n\overset{\text{O}}{\underset{\|}{\text{C}}}-$$

(wherein n stands for an integer in the range of 1 to 17), or a peptide residue formed by peptide linkage of two to ten amino acid residues of at least one species selected from the class mentioned above, and Z stands for one member selected from the class consisting of hydroxyl group and amino group.

2. An adsorbent according to claim 1, wherein said adsorbent is produced by subjecting said peptide immobilized on said carrier to heat treatment.

3. An adsorbent according to claim 1, wherein two cysteinyl mercapto groups in the Cys-Cys moiety of said formula are interlinked to each other to form a disulfide bond.

4. An adsorbent according to claim 1, wherein the peptide residues represented by X and Y are each one member selected from the group consisting of —Asp—Asp—, —Glu—Glu—, —Lys—Lys—, —Gly—Gly—, (NH(CH₂)₁₁C(=O))₂, (NH(CH₂)₁₇C(=O))₂, —Asp—Glu—, —Asp—Gly—, —Glu—Asp—, —Glu—Lys—, —Lys—Glu—, —Lys—NH(CH₂)₁₁C(=O)—, —Gly—Asp—, —Gly—Lys—, —NH(CH₂)₁₁C(=O)—Glu—, —NH(CH₂)₁₁C(=O)—Lys—, —NH(CH₂)₁₇C(=O)—Asp—, —NH(CH₂)₁₇C(=O)—Lys—, —Lys—Lys—Gly—, (Asp)₅, (Glu)₅, (Lys)₅, (Gly)₅, (NH(CH₂)₁₁C(=O))₅, (NH(CH₂)₁₇C(=O))₅, —Lys—Asp—Glu—Gly—NH(CH₂)₁₇C(=O)—, —Gly—Lys—Glu—Glu—Asp—, —Asp—Glu—NH(CH₂)₁₇C(=O)—Lys—Gly—Lys—, (Asp)₁₀, (Glu)₁₀, (Lys)₁₀, (Gly)₁₀, (NH(CH₂)₁₁C(=O))₁₀, (NH(CH₂)₁₇C(=O))₁₀, —Lys—Glu—Gly—NH(CH₂)₁₁C(=O)—Asp—Asp—Lys—Lys—Glu—Gly—, and —Lys—Glu—Glu—Gly—Asp—Asp—Lys—Lys—Gly—Gly—.

* * * * *